US010194800B2

United States Patent
Simons-Nikolova et al.

(10) Patent No.: US 10,194,800 B2
(45) Date of Patent: Feb. 5, 2019

(54) REMOTE PATIENT MANAGEMENT SYSTEM ADAPTED FOR GENERATING AN ASSESSMENT CONTENT ELEMENT

(75) Inventors: Mariana Simons-Nikolova, Bolton, MA (US); Johan Muskens, Eindhoven (NL); Armin Bruege, Boeblingen (DE)

(73) Assignee: Koninklijke Philips N.V., Eindhoven (NL)

( * ) Notice: Subject to any disclaimer, the term of this patent is extended or adjusted under 35 U.S.C. 154(b) by 937 days.

(21) Appl. No.: 12/985,356

(22) Filed: Jan. 6, 2011

(65) Prior Publication Data

US 2011/0172499 A1    Jul. 14, 2011

Related U.S. Application Data

(60) Provisional application No. 61/293,272, filed on Jan. 8, 2010.

(51) Int. Cl.
| | |
|---|---|
| *A61B 5/00* | (2006.01) |
| *G06F 19/00* | (2018.01) |
| *G16H 50/30* | (2018.01) |
| *A61B 5/022* | (2006.01) |
| *A61B 5/145* | (2006.01) |
| *G16H 10/20* | (2018.01) |
| *G16H 40/63* | (2018.01) |

(52) U.S. Cl.
CPC ............ *A61B 5/0002* (2013.01); *G06F 19/00* (2013.01); *G06F 19/3418* (2013.01); *G16H 50/30* (2018.01); *A61B 5/022* (2013.01); *A61B 5/14532* (2013.01); *A61B 5/4833* (2013.01); *G16H 10/20* (2018.01); *G16H 40/63* (2018.01)

(58) Field of Classification Search
CPC .............. A61B 5/0002; G06F 19/3418; G06F 19/3431
USPC .......................... 434/262, 323, 322; 600/300
See application file for complete search history.

(56) References Cited

U.S. PATENT DOCUMENTS

| | | | | |
|---|---|---|---|---|
| 6,039,688 A | * | 3/2000 | Douglas et al. | ............... 600/300 |
| 6,171,112 B1 | * | 1/2001 | Clark et al. | .................... 434/322 |

(Continued)

FOREIGN PATENT DOCUMENTS

| | | |
|---|---|---|
| WO | WO2007049163 | 5/2007 |
| WO | WO2007117719 | 10/2007 |

OTHER PUBLICATIONS

Computer Aided Environment for Generating Multiple Choice Test Items: Ruslan Mitkov, Cambridge University Press, Nov. 25, 2005.*

(Continued)

*Primary Examiner* — Robert J Utama
*Assistant Examiner* — Michael Humphrey

(57) ABSTRACT

The invention provides for remote patient management system comprising a computing device comprising a processor. The computing device further comprises a computer-readable storage medium containing instructions that when executed cause the processor to perform a method of calculating an assessment score. The assessment score measures the effect of a content element on a patient. The method comprising the steps of: delivering the content element to the patient, wherein the content element comprises a list of assessment parameters; generating an assessment content element using the list of assessment parameters; delivering the assessment content element to the patient; receiving a response from patient; and calculating the assessment score using the response.

19 Claims, 19 Drawing Sheets

(56) References Cited

U.S. PATENT DOCUMENTS

| | | | |
|---|---|---|---|
| 6,636,238 B1* | 10/2003 | Amir et al. | 715/730 |
| 6,769,915 B2* | 8/2004 | Murgia et al. | 434/236 |
| 7,228,315 B2* | 6/2007 | Finitzo et al. | |
| 7,260,480 B1 | 8/2007 | Brown et al. | |
| 7,668,718 B2* | 2/2010 | Kahn et al. | 704/270 |
| 7,970,628 B2* | 6/2011 | Kuo et al. | 705/2 |
| 2003/0022141 A1* | 1/2003 | Packard | 434/262 |
| 2003/0069752 A1* | 4/2003 | LeDain et al. | 705/2 |
| 2004/0107118 A1* | 6/2004 | Harnsberger et al. | 705/2 |
| 2004/0260155 A1* | 12/2004 | Ciarniello et al. | 600/300 |
| 2005/0137466 A1* | 6/2005 | Somov et al. | 600/300 |
| 2005/0233287 A1* | 10/2005 | Bulatov et al. | 434/114 |
| 2006/0212897 A1* | 9/2006 | Li et al. | 725/32 |
| 2008/0027292 A1* | 1/2008 | Rosman | G06F 19/323 600/300 |
| 2008/0189133 A1* | 8/2008 | Wilson et al. | 705/2 |
| 2009/0055221 A1 | 2/2009 | Loftus et al. | |
| 2011/0161107 A1* | 6/2011 | Goldberg et al. | 705/3 |

OTHER PUBLICATIONS

Bob Lewin et al., "The Heart Failure Plan", pp. 44-45, the British Heart Foundation, 2005.

* cited by examiner

| Patient's parameters | Validated Questionnaires | Purpose of the questions |
|---|---|---|
| Knowledge | Dutch HF knowledge questionnaire | Check knowledge level and changes therein |
| Beliefs | Beliefs about Compliance Scale | Check beliefs on barriers & benefits and changes therein |
| Compliance | Medication Event Monitoring System (MEMS)<br><br>Food Diary | Check compliance to medications and lifestyle and changes |
| Self-care behavior | European HF self-care behavior scale | Check self-care behavior and changes therein |
| Depression | CES-D, PHQ-9 | Screening for depression |
| Quality of life | WHO5, Minnesota Living with HF Questionnaire | Check quality of life parameters |

FIG. 4

| Question # | Q technique | Question text template examples |
|---|---|---|
| Q1 | QT1 | What kind of diet should you follow? |
| | | Why is a high blood pressure a problem? |
| | | What are the main side effects of diuretics? |
| Q2 | QT2 | How relevant is the <statement> for you? |
| | | What does it mean <phrase/noun>? |
| | | What is < phrase/noun >? |
| Q3 | QT3 | Is it important to ...? |
| | | Is it recommended to ...? |

FIG. 9

| Questions | Answer # | A technique | Answer text template examples | Purpose of the answer | Score |
|---|---|---|---|---|---|
| Q1 | | | | To check for: | |
| | A1 | AT1 | Yes/True | Sufficient knowledge | 3 |
| | A2 | | No/False | Missing knowledge and the patient is unaware | 0 |
| | A3 | | I don't know | Missing knowledge and the patient is aware | 1 |
| Q2 | | | | To rate: | |
| | A1 | AT2 | Very important | The importance of a specific statement on a 5 points Likert scale, for example ranging from *very important*, to *important, neutral, unimportant, and very unimportant* | 4 |
| | A2 | | Important | | 3 |
| | A3 | | Neutral | | 2 |
| | A4 | | Unimportant | | 1 |
| | A5 | | Very unimportant | | 0 |
| Q3 | | | | To check for: | |
| | A1 | AT3 | Partly correct 1 | Partial knowledge | 2 |
| | A2 | | Partly correct 2 | Partial knowledge | 2 |
| | A3 | | Partly correct 3 | Partial knowledge | 2 |
| | A4 | | Fully correct | Full knowledge | 3 |
| | A5 | | Fully incorrect | Missing knowledge and the patient is unaware | 0 |
| | A6 | | I don't know | Missing knowledge and the patient is aware | 1 |

FIG. 10

| Questions | Answer text template | Feedback # | F technique | Feedback text template examples | Purpose of the feedback |
|---|---|---|---|---|---|
| Q1 | Yes/True | F1 | FT1 | That is right! Sum up the answer | Give positive reward and reinforce knowledge |
| | No/False | F2 | FT3 | Sum up Q1 and provide the correct answer | Increase knowledge |
| | I don't know | F3 | FT4 | = F2 | Increase knowledge |
| Q2 | Very important | F1 | FT1 | That is right! Sum up the answer | Give positive reward and reinforce knowledge |
| | Important | F2 | FT1 | That is right! Sum up the answer | Give positive reward and reinforce knowledge |
| | Neutral | F3 | FT4 | Sum up Q2 and provide fully correct answer. | Increase knowledge |
| | Unimportant | F4 | FT3 | Sum up Q2 and provide fully correct answer. | Increase knowledge |
| | Very unimportant | F5 | FT3 | Sum up Q2 and provide fully correct answer. | Increase knowledge |
| Q3 | Partly correct 1 | F1 | FT2 | This answer is partly correct! Sum up the fully correct answer. | Give positive reward for the partly correct answer and increase knowledge |
| | Partly correct 2 | F2 | FT2 | = F1 | =F1 |
| | Partly correct 3 | F3 | FT2 | = F1 | =F1 |
| | Fully correct | F4 | FT1 | That is right! Sum up the answer. | Give positive reward and reinforce knowledge |
| | Fully incorrect | F5 | FT3 | Sum up Q3 and provide fully correct answer. | Increase knowledge |
| | I don't know | F6 | FT4 | Sum up Q3 and provide fully correct answer. | Increase knowledge |

Column headers: 1100, 1102, 1104, 1106, 1108, 1110

FIG. 11

| Input for | ContEI analysis | Frequency | Layout– B,*I*, U | Position in caption, heading 1, 2, 3, pane, |
|---|---|---|---|---|
| Question engine | Questions | | | |
| | Q1: What is blood pressure? | 1 | B | Heading 2 |
| | Q2: Why a high blood pressure is a problem? | 1 | B | Heading 2 |
| | Q3: Why do people get high blood pressure? | 1 | B | Heading 2 |
| | Q4: Is there anything I can do to manage my blood pressure? | 1 | B | Heading 2 |
| | Q5: Are there any particular foods I should be eating more of, or less of, to help my blood pressure? | 1 | B | Heading 2 |
| | Noun | | | |
| | N1: arteries | 3 | | |
| | N2: tubes | 1 | | |
| | N3: blood | 3 | | |
| | N4: heart | 4 | | |
| | N5: body | 2 | | |
| | N6: amount | 1 | | |
| | N7: pressure | 3 | | |
| | N8: pump | 1 | | |
| | N9: hypertension | 1 | *I* | |
| | N10: doctor | 1 | | |
| | N11: nurse | 1 | | |
| | N12: beat | 1 | | |
| | N13: contraction | 1 | | |
| | N14: diabetes | 1 | | |
| | N15: name | 1 | | |
| | N16: damage | 2 | | |
| | N17: organs | 1 | | |
| | N18: lining | 1 | | |
| | N19: problems | 2 | | |
| | N20: stroke | 1 | | |
| | N21: walls | 1 | | |
| | N22: elasticity | 1 | | |

FIG. 12A

| | | 800 | 806 | 808 | 810 | 812 |
|---|---|---|---|---|---|---|
| | | N23: pills | 1 | | |
| | | N24: risk | 1 | | |
| | | N25: diet | 2 | | |
| | | N26: salt | 2 | | |
| | | N27: health | 1 | | |
| | | N28: foods | 1 | | |
| | | N29: fruits | 1 | | |
| | | N30: vegetables | 1 | | |
| | | N31: wholegrain | 1 | | |
| | | N32: fish | 1 | | |
| | | N33: poultry | | | |
| 802 | | Phrases | | | |
| | | P1: high blood pressure | 10 | *I* | headings, Q2, Q3 |
| | | P2: blood pressure | 12 | | capture, headings, Q1, Q4, Q5 |
| | | P3: recommended blood pressure | 1 | | Beginning of a paragraph |
| | | P4: systolic pressure | 1 | B | in a bullet list |
| | | P5: diastolic pressure | 1 | B | in a bullet list |
| | | P6: heart disease | 1 | | paragraph |
| | | P7: kidney problems | 1 | | paragraph |
| | | P8: blood vessels | 1 | | |
| | | P9: fluid balance | 1 | | |
| | | P10: alcohol intake | 1 | | |
| | | Specific statement | | | |
| | | S1: That is why it is important to ... | 1 | | paragraph |
| | | S2: The recommended blood pressure is ... | 1 | | paragraph |
| 804 | Answer engine | Bullet lists | | | |
| | | • The first figure is the highest pressure ...<br>• The second figure is the lowest pressure | 1 | | Bullet list proceeded by complete sentence |
| | | • Eating a healthy heart diet<br>• Managing your fluid balance<br>• ...<br>• Looking after your general health | 1 | | Bullet list proceeded by incomplete sentence |

FIG. 12B

| 1300 | 1302 | 1304 | 1306 | 1308 | 1310 | 1312 | 1314 |
|---|---|---|---|---|---|---|---|
| 1 | 2 | 3 | 4 | 5 | 6 | 7 | 8 |
| Question # | Answer # | Answer technique | Answer text | Feedback # (Feedback technique used) | Feedback text | Go to Qn | Score |
| Q1 | \multicolumn{7}{l}{What is blood pressure? (generated via QT 1)} | | | | | | |
| | A1 | | The pressure of the blood in my heart. | F1 (FT 3) | It is not the pressure of the blood in your heart but in your arteries. | Q2 | 0 |
| | A2 | AT2 | The pressure of the blood in my arteries | F2 (FT 1) | That is right! | Q2 | 3 |
| | A3 | | I don't know | F3 (FT 4) | It is the pressure of the blood in your arteries. | Q2 | 1 |
| Q2 | Your blood pressure today is 140/85 mmHg. What does it mean? (generated via QT 2) | | | | | | |
| | A1 | | My highest pressure is 140 and my lowest pressure is 85. | F1 (FT 1) | That is right! | Q3 | 3 |
| | A2 | AT2 | My highest pressure is 85 and my lowest pressure is 140. | F2 (FT 3) | The correct answer is: your highest pressure is 140 and your lowest pressure is 85. | Q3 | 0 |
| | A3 | | I don't know | F3 (FT 4) | Your highest pressure is 140 and your lowest pressure is 85. | Q3 | 1 |
| Q3 | What does it mean systolic pressure? (generated via QT 2) | | | | | | |
| | A1 | | The pressure when the beat of the heart forces blood around the body. | F1 (FT 1) | Very well! | Q4 | 3 |
| | A2 | AT2 | The pressure between heartbeats when the heart is resting. | F2 (FT 3) | Systolic is the pressure when the beat of the heart forces blood around the body. | Q4 | 0 |
| | A3 | | I don't know | F3 (FT 4) | Systolic is the pressure when the beat of the heart forces blood | Q4 | 1 |

FIG. 13A 1300 1302 1304   1306        1308              1310            1312 1314

| Q4 | What does it mean diastolic pressure? (generated via QT 2) ||||||
|---|---|---|---|---|---|---|
| | A1 | | The pressure when the beat of the heart forces blood around the body. | F1 (FT 3) | Diastolic is the pressure between heartbeats when the heart is resting. | Q5 | 0 |
| | A2 | AT2 | The pressure between heartbeats when the heart is resting. | F2 (FT 1) | Well done! | Q5 | 3 |
| | A3 | | I don't know | F3 (FT 4) | Diastolic is the pressure between heartbeats when the heart is resting. | Q5 | 1 |
| Q5 | What is the recommended blood pressure? (generated via QT 3) |||||||
| | A1 | | Below 145/80 mmHg | F1 (FT 2) | Almost right! It is below 140/85 mmHg. | Q6 | 2 |
| | A2 | AT2 | Above 90/60 mmHg | F2 (FT 3) | No, it is below 140/85 mmHg. | Q6 | 0 |
| | A3 | | Below 140/85 mmHg | F3 (FT 1) | That is right! | Q6 | 3 |
| | A4 | | I don't know | F4 (FT 4) | It is below 140/85 mmHg. | Q6 | 1 |
| Q6 | What does it mean hypertension? (generated via QT 2) |||||||
| | A1 | | Low blood pressure - it stays down all the time. | F1 (FT 3) | Hypertension means high blood pressure, i.e., it stays up all the time. | Q7 | 0 |
| | A2 | AT2 | High blood pressure - it stays up all the time. | F2 (FT 1) | Very good! | Q7 | 3 |
| | A3 | | It goes up and down during the day. | F3 (FT 2) | Almost right! It doesn't go down, it stays up all the time. | Q7 | 2 |
| | A4 | | I don't know | F4 (FT 4) | Hypertension means high blood pressure, i.e., it stays up all the time. | Q7 | 1 |

FIG. 13B

| 1300 | 1302 | 1304 | 1306 | 1308 | 1310 | 1312 | 1314 |
|---|---|---|---|---|---|---|---|
| Q7 | Why is high blood pressure a problem? (generated via QT 1) | | | | | | |
| | A1 | AT2 | It can lead to stroke | F1 (FT 2) | Almost right! In addition to stroke, high blood pressure can lead to kidney problems and heart disease. | Q8 | 2 |
| | A2 | | It can lead to kidney problems | F2 (FT 2) | Almost right! In addition to kidney problems, high blood pressure can lead to stroke and heart disease. | Q8 | 2 |
| | A3 | | It can lead to heart disease | F3 (FT 2) | Almost right! In addition to heart disease, high blood pressure can lead to stroke and kidney problems | Q8 | 2 |
| | A4 | | It can lead to all above mentioned | F4 (FT 1) | Good answer! | Q8 | 3 |
| | A5 | | It does not harm | F5 (FT 3) | In fact, it does. If the blood pressure is high it can lead to kidney problems, stroke and heart disease. | Q8 | 0 |
| | A6 | | I don't know | F6 (FT 4) | If the blood pressure is high it can lead to kidney problems, stroke and heart disease. | Q8 | 1 |
| Q8 | Why do people get high blood pressure? (generated via QT 1) | | | | | | |
| | A1 | AT2 | If the walls of the larger arteries lose their natural elasticity and become rigid. | F1 (FT 2) | This is one of the reasons! Another one is if the smaller blood vessels become narrower. | Q9 | 2 |
| | A2 | | If the smaller blood vessels become narrower | F2 (FT 2) | This is one of the reasons! Another one is if the walls of the larger arteries lose their natural elasticity and become rigid. | Q9 | 2 |
| | A3 | | If A1) and/or A2) happened | F3 (FT 1) | That is right! | Q9 | 3 |
| | A4 | | Eating too much | F4 (FT 3) | No, high blood pressure develops if the walls of the larger arteries lose their natural elasticity and become rigid and if the smaller blood vessels become narrower. | Q9 | 0 |

FIG. 13C

| 1300 | 1302 | 1304 | 1306 | 1308 | 1310 | 1312 | 1314 |
|---|---|---|---|---|---|---|---|
| | | A5 | I don't know | F5 (FT 4) | High blood pressure develops if the walls of the larger arteries lose their natural elasticity and become rigid, and if the smaller blood vessels become narrower. | Q9 | 1 |
| Q9 | Is it important to check your blood pressure regularly? (generated via QT 3) | | | | | | |
| | | A1 | No, only when I feel there is a problem. | F1 (FT 3) | Yes, it's important to check your blood pressure regularly since the problems caused by high blood pressure are usually silent. | Q10 | 0 |
| | | A2 | AT2 | Yes, since the problems caused by high blood pressure are usually silent. | F2 (FT 1) | Very good! | Q10 | 3 |
| | | A3 | I don't know | F3 (FT 4) | It's important to check your blood pressure regularly since the problems caused by high blood pressure are usually silent. | Q10 | 1 |
| Q10 | What can you do to manage your high blood pressure? (generated via QT 1) | | | | | | |
| | | A1 | Take the right pills | F1 (FT 2) | Partly right! In addition to taking the right pill, you can manage your high blood by eating healthy diet, manage fluid balance, limit alcohol intake, no smoking and keep physically active. | Q11 | 2 |
| | | A2 | AT3 | Eat healthy diet | F2 (FT 2) | Partly right! In addition to eating healthy diet, you can manage your high blood by taking the right pills, manage fluid balance, limit alcohol intake, no smoking and keep physically active. | Q11 | 2 |
| | | A3 | Manage fluid balance | F3 (FT 2) | Partly right! In addition to fluid balance, you can manage your high blood by taking the right pills, eating healthy diet, limit alcohol intake, no smoking and keep physically active. | Q11 | 2 |

FIG. 13D

| 1300 | 1302 | 1304 | 1306 | 1308 | 1310 | 1312 | 1314 |
|---|---|---|---|---|---|---|---|
| | A4 | | Limit alcohol intake | F4 (FT 2) | Partly right! In addition tdimit alcohol intake, you can manage your high blood by taking the right pills, eating healthy diet, manage fluid balance, no smoking and keep physically active. | Q11 | 2 |
| | A5 | | No smoking | F5 (FT 2) | Partly right! In addition to no smoking, you can manage your high blood by taking the right pills, eating healthy diet, manage fluid balance, limit alcohol intake and keep physically active. | Q11 | 2 |
| | A6 | | Keep physically active | F6 (FT 2) | Partly right! In addition to , physical activity you can manage your high blood by taking the right pills, eating healthy diet, manage fluid balance, limit alcohol intake and no smoking. | Q11 | 2 |
| | A7 | | All of the above mentioned | F7 (FT 1) | Fully correct! Well done! | Q11 | 3 |
| | A8 | | Limit my working hours | F8 (FT 3) | Most important is to take the right pill, to eat healthy diet, manage fluid balance, limit alcohol intake, no smoking and keep physically active. | Q11 | 0 |
| | A9 | | I don't know | F9 (FT 4) | You can manage your high blood pressure if you take the right pill, eat healthy diet, manage fluid balance, limit alcohol intake, no smoking and keep physically active. | Q11 | 1 |
| Q11 | What kind of diet will help you to reduce the risk of developing a high blood pressure? (generated via QT 1) | | | | | | |

FIG. 13E

| 1300 | 1302 | 1304 | 1306 | 1308 | 1310 | 1312 | 1314 |
|---|---|---|---|---|---|---|---|
|  | A1 | AT2 | a low carbs diet | F1 (FT 3) | That is not right! A combination of a low sodium diet, diet high in vegetables and fruits and diet rich in wholegrain products, fish and poultry, reduces the risk of developing a high blood pressure. |  | 0 |
|  | A2 |  | a low sodium diet | F2 (FT 2) | Partly right! In addition to low sodium diet, diet high in vegetables and fruits and diet rich in wholegrain products, fish and poultry, reduces the risk of developing a high blood pressure. |  | 2 |
|  | A3 |  | a diet high in vegetables and fruits | F3 (FT 2) | Partly right! In addition to diet high in vegetables and fruits, a low sodium diet and a diet rich in wholegrain products, fish and poultry, reduces the risk of developing a high blood pressure. |  | 2 |
|  | A4 |  | diet rich in wholegrain products, fish and poultry | F4 (FT 2) | Partly right! In addition to a diet rich in wholegrain products, fish and poultry, a diet high in vegetables and fruits, and a low sodium diet reduce the risk of developing a high blood pressure. |  | 2 |
|  | A5 |  | a combination of a, b, c | F5 (FT 3) | A combination of a low sodium diet, diet high in vegetables and fruits and diet rich in wholegrain products, fish and poultry, reduces the risk of developing a high blood pressure. |  | 0 |
|  | A6 |  | a combination of b, c, d | F6 (FT 2) | That is right! |  | 3 |
|  | A7 |  | I don't know | F7 (FT 4) | A combination of a low sodium diet, diet high in vegetables and fruits and diet rich in wholegrain products, fish and poultry, reduces the risk of developing a high blood pressure. |  | 1 |

FIG. 13F

REMOTE PATIENT MANAGEMENT SYSTEM ADAPTED FOR GENERATING AN ASSESSMENT CONTENT ELEMENT

CROSS-REFERENCE TO RELATED APPLICATIONS

This patent application claims the priority benefit under 35 U.S.C. § 119(e) of U.S. Provisional Application No. 61/293,272 filed on Jan. 8, 2010, the contents of which are herein incorporated by reference.

TECHNICAL FIELD

The invention relates to remote patient management systems.

BACKGROUND OF THE INVENTION

The goal of the disease management programs such as heart failure, chronic obstructive pulmonary disease (COPD), diabetes, sleep apnea disease management programs, including those offered via remote patient management systems, is to empower patients to control their complex chronic condition. Similarly, lifestyle change programs such as weight management, smoking cessation, or physical activity programs are meant to empower consumers to change their behavior. The key component of both types of programs, i.e. disease management and lifestyle, is therefore coaching the patient. Coaching addresses the following:
  Improving knowledge about the chronic condition or specific aspects of these;
  Changing attitudes of the patients toward certain behaviors that they need to adopt in order to adhere to the prescribed medication and lifestyle goals;
  Guiding a patient through stages of change, e.g., from pre-contemplation, through contemplation, action and maintenance; and
  Removing perceived barriers and enforcing the benefits that a patient has toward the specific behavior or a goal.

Patient non-compliance decreases the efficacy of pharmacological and non-pharmacological therapy and exposes the patient to clinical destabilization, which can lead to exacerbating disease symptoms. Evidence from clinical trials and validated insights show that the most commonly identified cause of disease worsening, e.g. Heart Failure (HF) decompensation, is non-compliance with medication, low sodium diet, fluid restriction and physical activity. Non-compliance is the precipitating factor of exacerbation, leading to poor clinical outcomes. Therefore, interventions overcoming low patient compliance are needed.

The coaching of patients may be managed with so called remote patient management systems, which are also known as telehealth systems. The coaching of patients may be coded into executable care plans which may be executed by an application hosting device which the patient has access to. An application hosting device may present or deliver so-called content elements. A common way to assess the knowledge, compliance, self-care behavior, etc. of a patient is through questionnaires, e.g., surveys or quizzes. This is also true in many personal healthcare systems and approaches, where scientifically validate questionnaires are used to assess knowledge as well as other cognitive, behavioral and emotional parameters.

SUMMARY OF THE INVENTION

Scientifically validated questionnaires may not be suitable for measuring the effect of individual content elements in the patient's care plan on the patient's parameters. These questionnaires may not be tailored towards the effect of an individual content element (e.g., digestible pieces of information like video or a section of a patient's booklet) from the educational programs. Due to the enormous variety and the proprietary nature of the content elements the patient is exposed to, assessments that verify this effect (e.g., a quiz after a video) often are not available.

A content element as used herein is content which may be provided to a patient and which may be integrated into a care plan for the patient. A care plan is a day-to-day plan for managing a disease or health condition. Content elements may be provided either by a hospital or an outpatient clinic or a disease management organization or a remote patient management (RPM) system, resulting in the proprietary nature of the content elements as well as assessments. The generation of these assessments is time consuming and requires human expertise. As a result these assessments are not automatically available, leading to the unmet needs mentioned above.

Embodiments of the invention may address the above mentioned problem by implementing a system module of a remote patient management system that automatically generates assessments such as surveys and quizzes to verify the effect of a specific content element (e.g., video or a section of a patient's booklet) on patient's parameters like knowledge, beliefs on barriers and benefits, self-care, that influence patient's compliance. The system module may facilitates efficient creation of more effective education and coaching intervention. The efficiency is improved through automatic generation and scheduling of new content elements in the patient's care plan while the effectiveness of the intervention is high due to embedded capability in the system to assess whether the content elements are effective and if not to react thereon.

Patient's education and coaching is becoming more and more an important element of health interventions. The objective is that through education patients will become more compliant to a health intervention, since knowledge is one of the major determinants for compliance. This is illustrated by the following quotes of heart failure nurses during an insight session.

Unmet need 1: "Maximize the effect of education I provide"

We provide education to our patients during face-to-face consults. In addition, we give them a map with educational materials for home use. Often we repeat the information a couple of times until we see that the patient got the basics. Having tools for structural assessment of the effect of the education we provide are necessary to help us in identifying necessary improvements that will maximize the educational effect.

Unmet need 2: "Check the effect of education"

Our patients get educational material via a telehealth system, but we do not know 1) what the initial patient's knowledge level was and 2) what was the impact/effect of the educational material. For each patient we need to decide on personalized coaching with respect to medication and lifestyle interventions. The decision is based on patient's knowledge level (among others) and the effect of the already provided educational material. Thus, we need tools to check the effect of education.

Embodiments of the invention may include a software module named a Content Element Engine which:
  generates automatically assessment such as surveys and quizzes checking the effect of a content element (e.g., a video or a section of a patient's booklet) on patient's cognitive, behavioral and emotional parameters such as knowledge, believes, self-care management, etc.

expands a set of predefined content elements in the patients care plan with newly generated content elements such as surveys and quizzes. The latter are coupled to the existing content elements (e.g., a video or a section of a patient's booklet) that are marked with an attribute EPP=[list of desired patient's parameters to check]. EPP is equivalent to the term list of assessment parameters.

The Content Element Engine could be embedded in an authoring tool of a RPM system. The authoring tool could provide a list/catalog of teaching elements from a content library, filled by both—predefined content and content generated by the Content Element Engine. Then, the medical professionals could build the assessment tools themselves, e.g. a survey or a teaching quiz, by dragging/dropping content elements, automated creation of questions/answers/feedback via Content Element Engine based on behavioral models, pre-view of generated survey/quiz and the possibility for simulation and testing before it goes into the final steps—integration of those surveys and quizzes into an integrated care plan.

The invention provides for a remote patient management system comprising a computing device. The computing device comprises a processor. The computing device further comprises a computer-readable storage medium containing instructions that when executed cause the processor to perform a method of calculating an assessment score. A computer-readable storage medium as used herein is any storage medium which may be read by a computer or processor. Examples of computer-readable storage medium include but are not limited to: floppy disks, hard disks, solid state hard disk, USB thumb drives, RAM memory, ROM memory, EEPROM memory, and registers in processors or microprocessors. A remote patient management system is a system which may be used to both monitor a patient and also to manage the care of a patient. Remote patient management systems are also known as telehealth systems.

An assessment score as used herein is a ranking or scoring which assesses a patient's cognitive, behavioral, and/or an emotional parameter that is influenced by a content element. The assessment score measures the effect of a content element on a patient parameters such as the aforementioned cognitive, behavioral, and/or an emotional parameters. The method comprises the step of delivering the content element to the patient. The content element comprises a list of assessment parameters. The method further comprises the step of generating an assessment content element using the list of assessment parameters. This may include generating an assessment content element for each assessment parameter in the list. The method further comprises the step of delivering the assessment content element to the patient. The method further comprises the step of receiving a response from the patient. The method further comprises the step of calculating the assessment score using the response. An assessment parameter as used herein is a cognitive, behavioral, or emotional parameter of a patient which may be assessed or measured using a scientifically validated questionnaire. The term patient parameter as used herein is a synonym for assessment parameter.

In another embodiment the remote patient management system further comprises a home infrastructure device. A home infrastructure device as used herein is a device adapted for delivering the content element and the assessment content element to the patient. The home infrastructure device comprises a diagnostic medical device for measuring a value of a patient's vital sign. Patient vital signs are any physical property of the patient which may be measured. Examples of vital signs include, but are not limited to: weight, blood sugar level, blood pressure, pulse, SpO2, and bio-impedance.

The list of assessment parameters is appended with a supplementary assessment parameter if the value of the vital sign is outside of a predetermined range. A home infrastructure device as used herein is a device adapted for connecting or communicating with a computing device and reporting the value of a patient vital sign to the computing device. For instance a home infrastructure device may be a single diagnostic medical device that is connected or networked to the computing device. A home infrastructure device may also comprise an application hosting device. An application hosting device is a device with a processor that is able to execute a care plan. A care plan as used herein is a day-to-day plan for managing a disease or health condition. One or more diagnostic medical devices may be connected to the application hosting device. A feedback device for presenting information to a patient or receiving information from a patient may also be connected to the application hosting device. The application hosting device may receive measurements of patient vital signs from the diagnostic medical device. A home infrastructure device may also comprise an application hosting device which is connected or networked to the computing device in addition to a diagnostic medical device which is directly connected or networked to the computing device. This embodiment is advantageous because measurements of a vital sign which are outside of a predetermined range can trigger the assessment of a patient parameter which may be responsible for the vital sign being outside of the predetermined range. For instance if the measurement of a blood sugar level is outside of a predetermined range such as the blood sugar level is too high, the patient parameter such as compliance to sugar restricted diet could be checked.

In another embodiment the content element comprises a text where the step of generating an assessment content element comprises parsing the text into text elements. The text may depend upon the form of the content element. If the content element is text which is for display on a patient interface then the text is simply the text of the text document. If the content element is an audio file or a video with an audio file then the text may be a transcript of the audio portion of the audio file or of the video file. If the content element is an image or a video which contains text then the text would be a record of the text which is displayed in the image or images. The step of generating an assessment content element further comprises determining a frequency of each of the text elements. Text elements may be a variety of elements within a text. For instance a text element may be a question contained within the text. A text element may also be a noun contained within the text. A text element may also be a phrase contained within the text. A text element may also be a specific statement within the text. The step of generating an assessment content element further comprises selecting a candidate for question creation using the frequency of each of the text elements. The step of generating an assessment content element further comprises generating a question to create the assessment content element using the candidate. This embodiment is advantageous because a text can be automatically parsed and used to create an assessment content element.

In another embodiment the step of generating an assessment content element further comprises determining an emphasis for each of the text elements. An emphasis for a text element as used herein is defined as a change in font or emphasis of a text element with respect to the majority of text within a text document. For instance using a larger font, using a bold faced font, using an italics font, highlighting, changing font or underlining a text element may be used to indicate an emphasis for the text element. The step of generating a assessment content element further comprises determining a position for each of the text elements. A position for each of the text elements as used herein is defined as a position or location within the text document. This may indicate text being located in headings, bullet points, in a summary, or within a block of text. Determining a position for each of the text elements may be used to indicate the importance of a text element. For instance, if a text element is used within a chapter title or a section heading it may indicate that that particular text element is relevant. The step of selecting a candidate for question creation using the frequency of each of the text elements comprises using the emphasis and position for each of the text elements for the selection.

In another embodiment the questions created using any one of the following: using a question parsed from the text, inserting a parsed phrased or parsed noun into a question template, and reformulating a parsed statement into a question.

In another embodiment the step of generating a assessment content element further comprises generating a set of multiple choice answers for each of the a questions. This embodiment is advantageous because questions which may be used for performing assessment are generated automatically.

In another embodiment the set of multiple choice answers is generated using any one of the following: a multi-choice template for answering closed questions, a multi-choice template for answering open questions, and multiple choice answers generated from a bullet list detected during parsing the text into text elements.

In another embodiment the step of generating a assessment content element further comprises generating a feedback element for each answer of the set of multiple choice answers. The assessment content element may comprise the feedback element. A feedback element comprises content for coaching the patient towards desired behavior or reinforcing this behavior based on the response. A feedback element may be a content element or it may be a part of the assessment content element. In some embodiments a feedback element may be selected from a library of content elements.

In another embodiment the feedback element is generated using any one of the following: a correct answer feedback template, a partially correct answer feedback template, an incorrect answer feedback template, and an 'I don't know' answer feedback template. A template as used herein is a text which contains spaces for words or additional text to be inserted. When the additional words or additional text is inserted into the template complete sentences or statements are constructed.

These four types of templates are used to create feedback elements for the particular type of response. The names of the answer feedback templates are self-descriptive. For instance a correct answer feedback template indicates that the patient answered a question correctly. In this case the feedback is a combination of template, e.g., "That is right!" to reward the correct answer and then reinforce patients knowledge by summing up the answer. The same applies to the other three templates. For a partially correct answer feedback template, a feedback element is generated using this template for a response to a question where the answer was only partially correct. For an incorrect answer feedback template, a feedback element is generated using this template for a response to a question where the answer was not correct. For an "I don't know" answer feedback template, a feedback element is generated for this template when the answer was "I don't know" or was a statement equivalent to "I don't know."

In another embodiment the computer-readable storage medium further comprises instructions for implementing a voice-to-text generation module. The method further comprises at least partially generating the text using the voice-to-text generation module on any audio components of the content element. This embodiment is advantageous when the content element contains an audio component. If the content element comprises an audio component a transcript of the text may also be attached to it. However, this particular embodiment is able to automatically generate text using the audio component. This embodiment may therefore be used in the case where a content element has an audio component but does not have an attached transcript of the audio component.

In another embodiment the computer-readable storage medium further comprises instructions for implementing an optical character recognition module. The method further comprises at least partially generating the text using the optical character recognition module on any image components of the content element. For instance, the content element could be a brochure or text. Scanning the brochure or text will allow the optical character recognition module to provide a text. The optical character recognition module could also be used on images or on the images of a video which contain text.

In another embodiment the text elements are any one of the following: questions, phrases, nouns, specific statements, and bullet lists.

In another embodiment the computer-readable storage medium further comprises instructions for implementing a text-to-voice generation module. The method further comprises generating the assessment content element using the text-to-voice generation module. This embodiment is advantageous when an audio feedback is desired instead of a text assessment content element. For instance patients with poor eyesight may not be able to effectively read a quiz that is an assessment content element. However, one with poor eyesight would be able to listen to a quiz and possible responses to a quiz and then respond to the assessment content element.

In another embodiment the method further comprises the step of providing feedback based upon the response. Providing the feedback may be used to further reinforce the content element.

In another embodiment the assessment content is a quiz or a survey.

In another embodiment the assessment score is a measure of any one of the following: knowledge, self-care behavior, compliance and beliefs on barriers and benefits.

In another embodiment the content element is any one of the following: a message, a tip, an interactive message, a survey, a quiz, a medical video, a psychological video, a heart failure goal module, a diabetes goal module, games-for-health, symptoms checklists, recipes and an educational game.

In another embodiment the remote patient management system further comprises a home infrastructure device. The home infrastructure device comprises a diagnostic medical device for measuring the value of a vital sign. Calculation of the assessment score is based at least partially on a trend of the value of the vital sign. This embodiment is particularly advantageous because the assessment score is used to measure the effect of a content element on a patient. The trend of the value of the vital sign may be an indicator of the effect of the content element on a patient also. For instance, if the patient is a diabetic and has received a content element which explains the importance of maintaining a proper blood sugar level then the trend of the patient's blood sugar level may be a good indicator of the degree of compliance of the patient with the information in the content element.

In another aspect the invention provides for a computer-readable storage medium containing instructions that when executed by a processor of a computing device cause the computing device to perform a method of calculating an assessment score. The assessment score measures the effect of a content element on a patient. The method comprises delivering the content element to the patient. The content element comprises a list of assessment parameters. The method further comprises generating a assessment content element for each assessment parameter in the list. The method further comprises delivering the assessment content element to the patient. The method further comprises receiving a response from the patient. The method further comprises calculating the assessment score using the response.

In another aspect the invention provides for a computer-implemented method of calculating an assessment score by a remote patient management system, wherein the remote patient management system comprises a computing device with a processor for executing the method, wherein the assessment score measures the effect of a content element on a patient. The method comprises delivering the content element to the patient. The content element comprises a list of assessment parameters. The method further comprises generating a assessment content element using the list of assessment parameters. The method further comprises delivering the assessment content element to the patient. The method further comprises receiving a response from the patient. The method further comprises calculating the assessment score using the response.

BRIEF DESCRIPTION OF THE DRAWINGS

In the following preferred embodiments of the invention will be described, by way of example only, and with reference to the drawings in which:

FIG. 4 contains a table which lists various patient parameters;

FIG. 9 contains a table which illustrates three different techniques of using templates to construct questions;

FIG. 10 contains a table which illustrates an answer template which may be used for creating answers to questions;

FIG. 11 contains a table which illustrates a feedback template used for creating feedback to answers;

FIG. 12a contains a table identical to that shown in FIG. 8 that has been filled with text elements that have been parsed from a workbook;

FIG. 12b is a continuation of FIG. 12a;

FIG. 13a contains a table which shows a newly generated quiz created using the text elements from the table of FIGS. 12a and 12b;

FIG. 13b is a continuation of FIG. 13a;

FIG. 13c is a continuation of FIGS. 13a and 13b;

FIG. 13d is a continuation of FIGS. 13a through 13c;

FIG. 13e is a continuation of FIG. 13a through 13d; and

FIG. 13f is a continuation of FIG. 13a through 13e.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
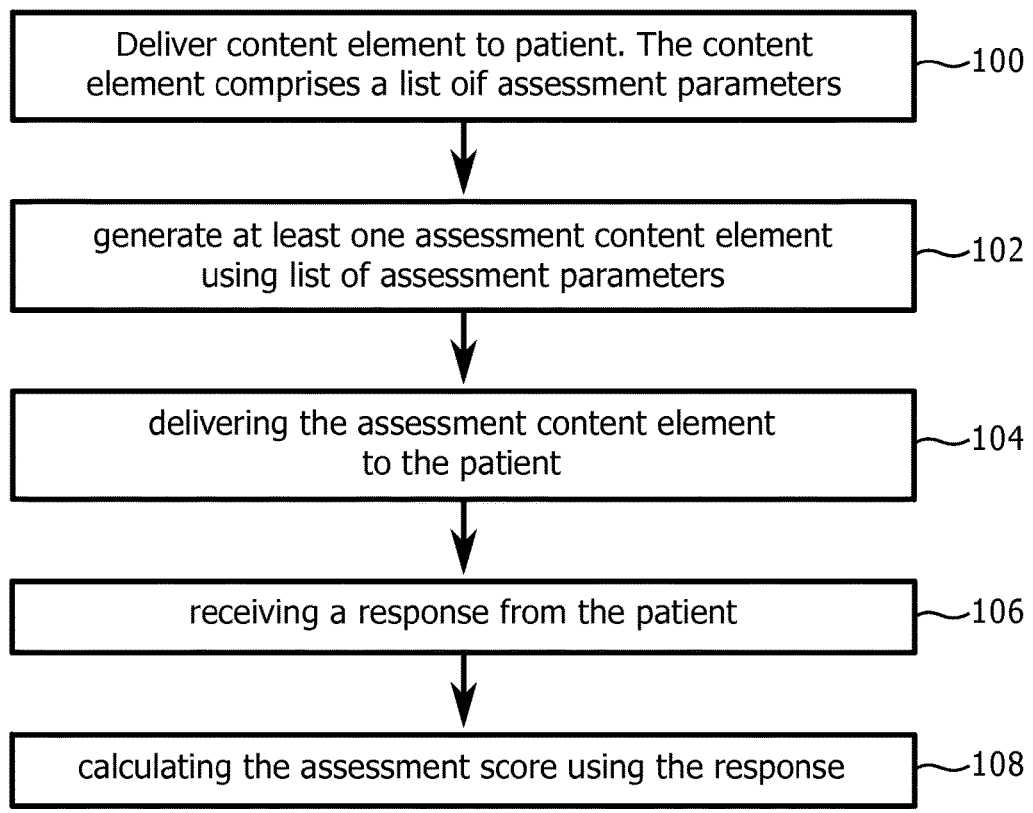
FIG. 1 shows a block diagram which illustrates an embodiment of the method according to the invention.

FIG. 1 shows a block diagram which illustrates an embodiment of the method according to the invention. In step 100 the content element is delivered to the patient. The content element comprises a list of assessment parameters. In step 102 an assessment content element is generated using a list of assessment parameters. In step 104 the assessment content element is delivered to the patient. In step 106 a response is received from the patient. In step 108 the assessment score is calculated using the response.

Figure 2:
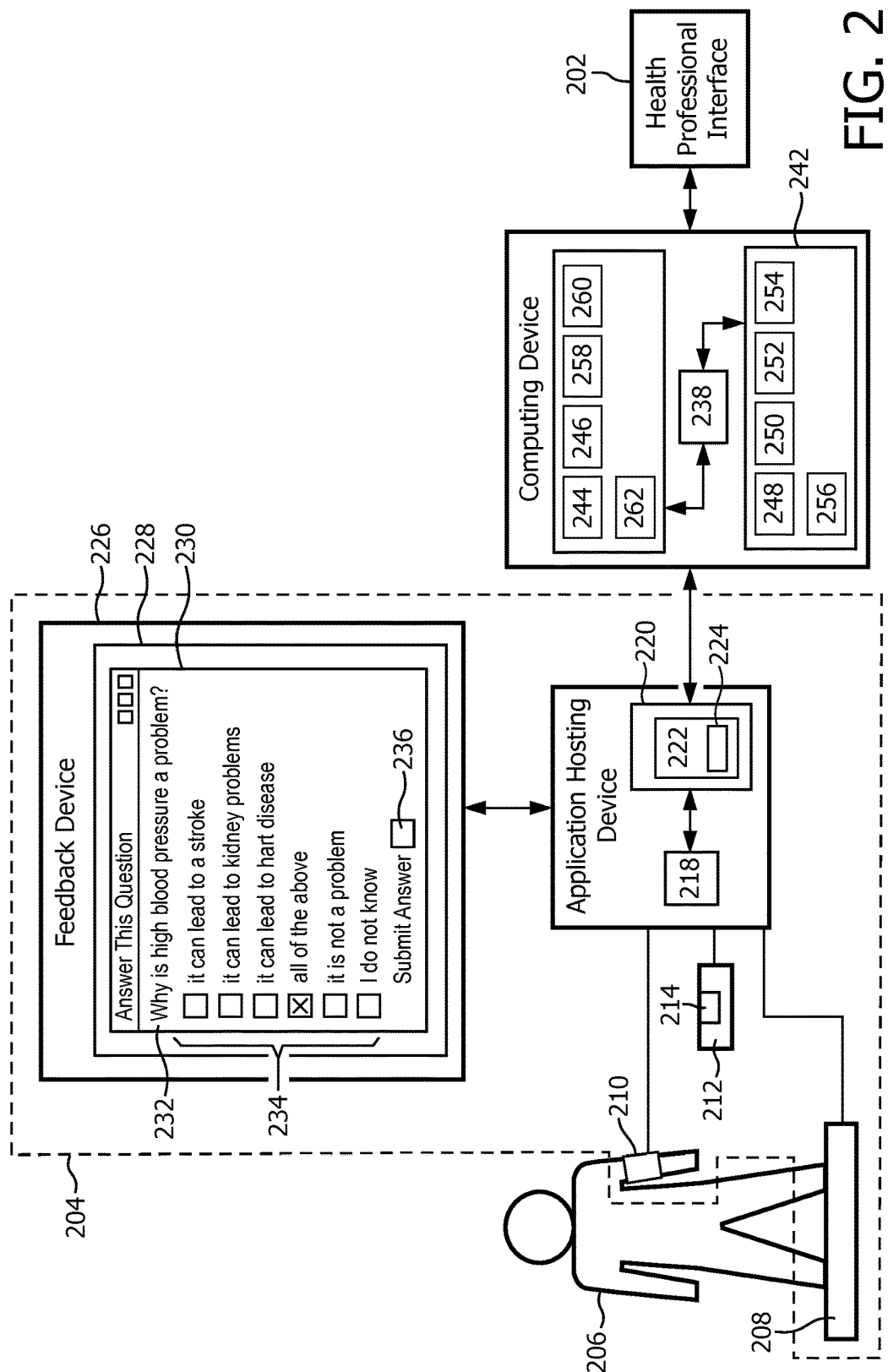
FIG. 2 shows a functional diagram which illustrates a remote patient management system.

FIG. 2 shows a functional diagram which illustrates a remote patient management system according to an embodiment of the invention. The remote patient management system comprises a computing device 200. The computing device is connected to a health professional interface 202. The health professional interface 202 is an interface or computer which is connected or networked to the computing device 200. The health professional interface 202 allows a health professional such as a physician, nurse or other care provider to manage the treatment of a patient 206 using the remote patient management system. The computing device 200 is also shown as being connected to a home infrastructure device 204. The home infrastructure device may comprise one or more vital sign measurement devices 208, 210, 212 for measuring vital signs of the patient 206.

In this embodiment the home infrastructure device 204 comprises a scale 208 measuring the weight of the patient 206, a blood pressure cuff 210 for measuring the blood pressure of the patient 206 and a blood sugar measurement device 212 for measuring the blood sugar of a blood sample 214 from the patient 206. All three of these diagnostic medical devices 208, 210, 212 are shown as being connected to an application hosting device 216. The application hosting device 216 comprises a processor 218 which is connected to a computer memory 220. The computer memory 220 is shown as comprising a care plan 222. The care plan 222 is an executable care plan which may be executed by the processor 218 and is used for managing a chronic health condition of the patient 206. The computer memory 220 also comprises an assessment content element 224 which is shown in this embodiment as being part of the care plan 222. In other embodiments, the assessment content element 224 may be separate from the care plan 222. The assessment content element 224 is used for calculating an assessment score to measure the effect of a content element 244 on the patient 206.

The application hosting device 216 is shown as being connected to a feedback device 226. A feedback device is a device which allows the patient 206 to interact with the application hosting device 216. The feedback device 226 may be integrated into the application hosting device 216 or they may be separate devices which are connected or networked. In this embodiment the feedback device 226 comprises a display 228. On the display 228 is shown a graphical user interface 230. Within the graphical user interface 230 a question 232 is displayed which is a part of the assessment content element 224. Below the question 232 is a set of possible answers with check boxes that allow the patient to select an answer to the question 232. Shown below the questions and check boxes 234 is a button 236 which allows the patient 206 to submit his or her response to the question 232.

The computing device 200 comprises a processor 238. The processor 238 is connected to computer storage 240 and computer memory 242. Computer memory 242 and Computer storage 240 are both examples of computer-readable storage medium. Computer memory 242 is any memory which is directly accessible to a processor. Examples of computer memory 242 include, but are not limited to: RAM memory, EEPROM memory, registers, and register files. Computer storage 240 is any computer-readable storage medium intended for long term data or program storage. Examples of computer storage include, but are not limited to: a hard disk drive, a USB thumb drive, a floppy drive, a smart card, a DVD, a CD-ROM, and a solid state hard drive.

Within the computer storage 240 is a content element 244. The content element 244 could also be stored by the application hosting device 216. The content element 244 could be delivered to the patient 206 by transferring a copy of the content element 244 to the application hosting device 216 or via the connection between the application hosting device 216 and the computing device 200 the content element 244 could be displayed directly to the patient 206 using the feedback device 226. Also within the storage 240 of the computing device 200 is an assessment content element 246. The assessment content element 246 has been generated for calculating an assessment score for content element 244 after it has been delivered to the patient 206.

Within the memory 242 of the computing device 200 is an assessment content element creation module 248. This module 248 is used for creating the assessment content element 246. Also within the memory 242 is a text-to-speech module. The text-to-speech module 250 is used for creating assessment content elements 246 which comprise audio instead of textual information. Within the memory 242 is also an optical character registration module 252. The optical character registration module 252 may be used to detect and identify text in images and in video clips. Within the memory 242 is also a speech-to-text module 254. The speech-to-text module 254 may be used to use an audio component of a content element 244 and turn it into a text which may be parsed for text elements according to an embodiment of the invention. Also within the memory 242 is a vital sign trend tracking module 256. The vital sign trend tracking module 256 is used for recording and/or identifying trends in vital sign measurements from the patient 206. Within the computer storage 240 a patient record 258 is located. This is a record of the patient's 206 medical history and/or recordings of vital sign measurements from the diagnostic medical devices 208, 210, 212 connected to the application hosting device 216. Also within the computer storage 240 there is a care plan library 262. These are care plans which may have been created for groups of or for individual patients 206. Also within the computer storage 240 is a multi-media content library 260. The multi-media content library 260 may be used for supplying content elements to the feedback device 226.

Figure 3:
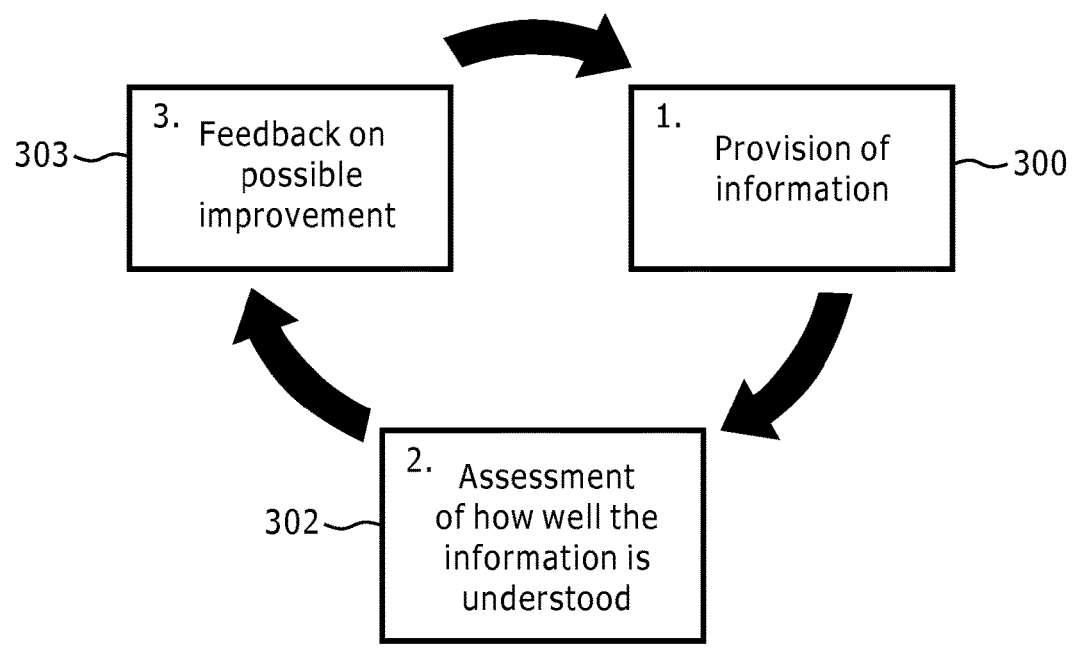
FIG. 3 shows a block diagram which illustrates an education program.

FIG. 3 shows a block diagram which illustrates an education program. In step 300 information is provided. In step 302 an assessment is made of how well the information is understood. In step 303 feedback is provided on possible improvement based upon the assessment 302. After the feedback 303 is provided the cycle starts again and information is again provided, step 300.

FIG. 4 shows a table with tools for assessing HF patient's cognitive, behavioral and emotional parameters. Column 400 shows a listing of different possible patient parameters. Column 402 shows validated questionnaires that are used to assess a particular patient parameter 400. Column 404 shows the purpose of the questions of the particular validated questionnaire 402. In other words in column 404 is shown what is measured by calculating an assessment score using a particular validated questionnaire 402. Taking an example from this table, the patient parameter for the Dutch heart failure knowledge questionnaire is knowledge. The purpose of this questionnaire is to check the patient knowledge level and changes therein with respect to heart failure.

Figure 5:
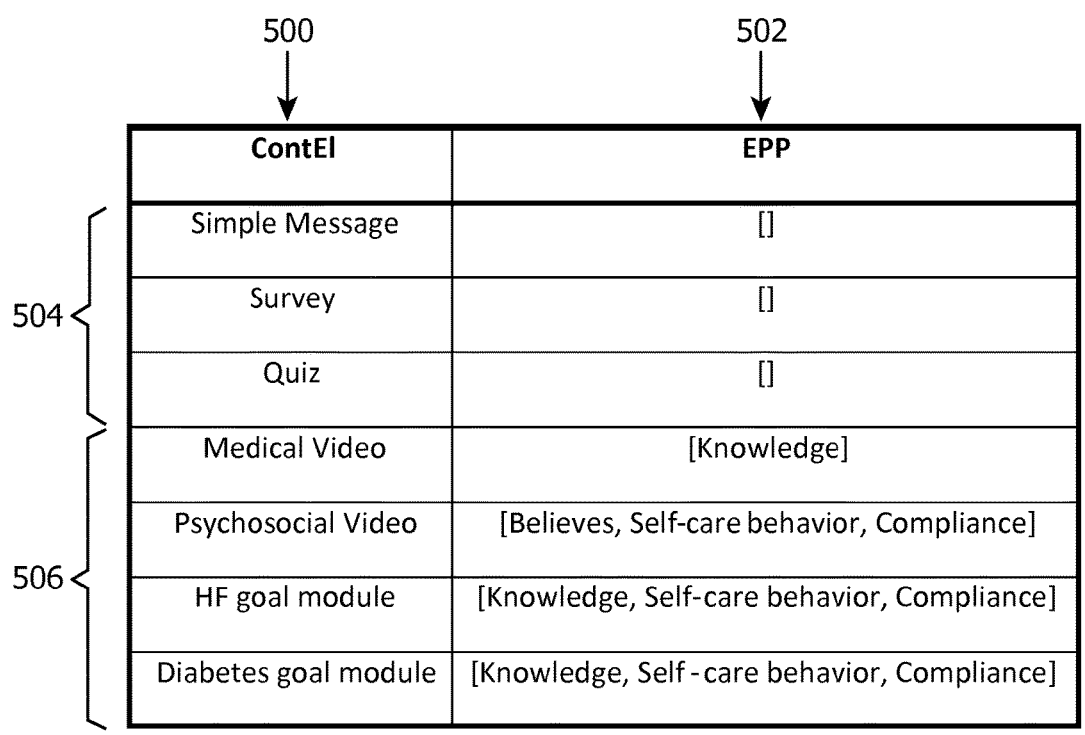
FIG. 5 contains a table which lists different types of content elements.

FIG. 5 shows a table listing different types of content elements in column 500. In column 502 a list of patient parameters on which the effect should be assessed is given. The list is called EPP (effect on patient's parameter). The content elements are divided into two groups. In group 504 there are content elements for which the list of assessment parameters is empty. For example the effect of a simple message on patient knowledge, compliance, etc., might be too restrictive to be assessed separately. A survey and a quiz are already assessment content elements, thus there is no need to create for them another assessment content elements. Within the second group 506 there are content elements which do comprise a list of assessment parameters. For example a medical video may have a list of assessment parameters which comprises only knowledge. In another example a heart failure goal module may have a list of assessment parameters which comprises knowledge, self-care behavior, and compliance.

Figure 6:
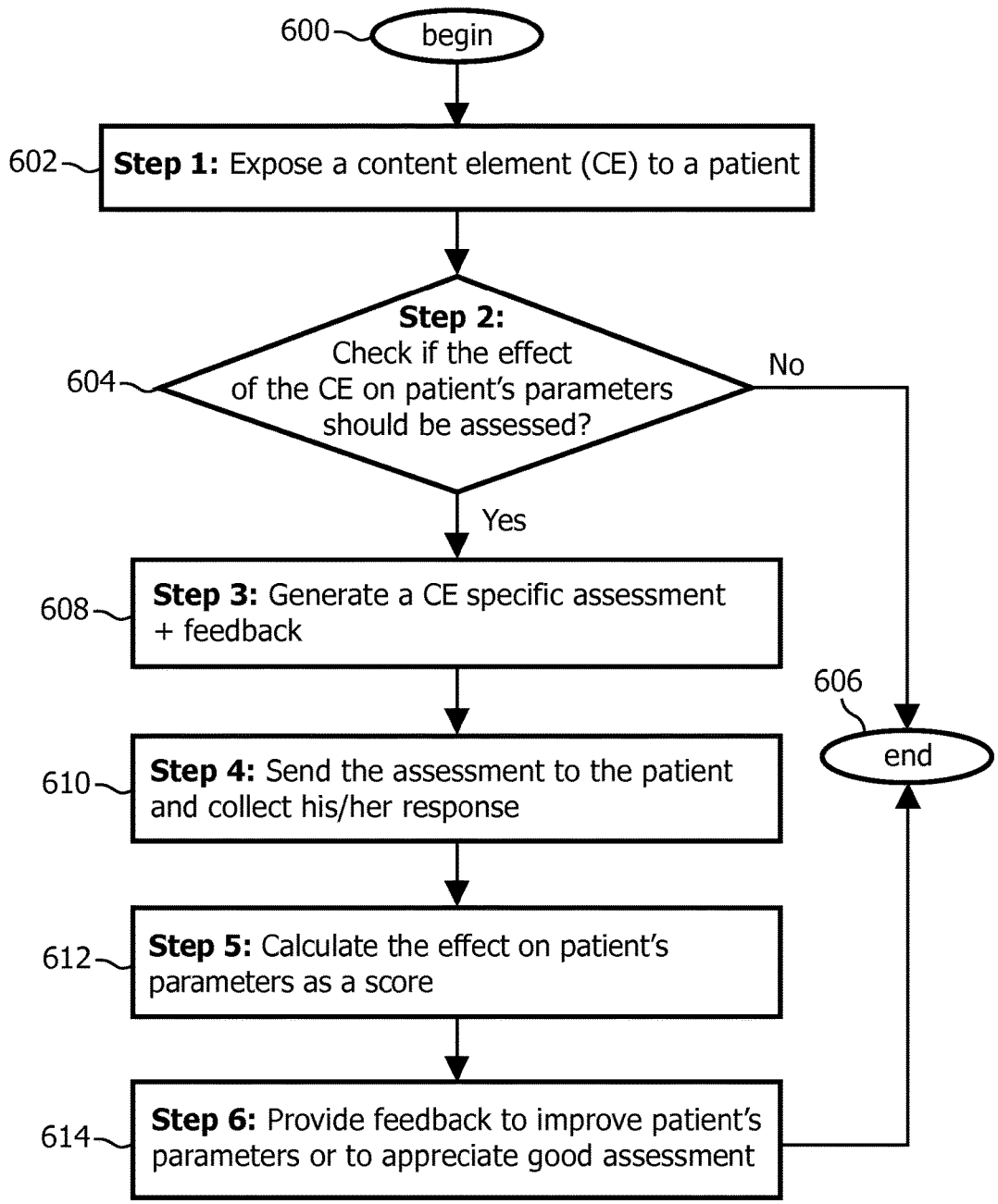
FIG. 6 shows a flow diagram which illustrates an embodiment of the method according to the invention.

FIG. 6 shows a flow diagram which illustrates an embodiment of the method according to the invention. In step 600 the method begins. In step 602 a content element is exposed or delivered to a patient. In step 604 a determination is made if the effect of the content element on a patient's parameters should be addressed. For instance if the content element comprises a list of assessment parameters which is empty then no assessment is made. In this case the method ends at step 606. If the content element however does comprise a list of assessment parameters then the method continues to step 608. In step 608 a content element specific assessment and feedback are generated. This is the generation of the assessment content element.

Step 608 may be performed by a content element (ContEl) engine. The content element engine takes as an input:

I1. a content element from the patient's specific care plan with non-empty EPP list, e.g., a video or a section of a patient's booklet;

I2. a patient's vital(s) that will be used to personalize the generated assessment and feedback.

It generates as an output a content element that provides either O1) and/or O2):

O1. assessment of
 a. patient's cognitive, behavioral and emotional parameters, triggered by the input content elements as well as
 b. changes in these parameters;

O2. feedback for improvement of the patient's parameters mentioned above.

An example of a content element that provides only O1) is a survey while a teaching quiz covers both O1) and O2). Summing up, the content element engine expands the set of content elements in the patient's care plan with automatically generated surveys or teaching quizzes (new content elements) coupled to existing content elements with non empty Effect on Patient Parameter (EPP) list. An EPP list is another wording for a list of assessment parameters.

In step 610 the assessment content element is sent to the patient and a response is collected from the patient. In step 612 the effect on a patient's parameter is calculated as a score. This is the step of calculating the assessment score using the response. In step 614 feedback is provided to the patient to improve the patient's parameters or to provide positive feedback for a good assessment. After step 614 the method ends at step 606.

Figure 7:
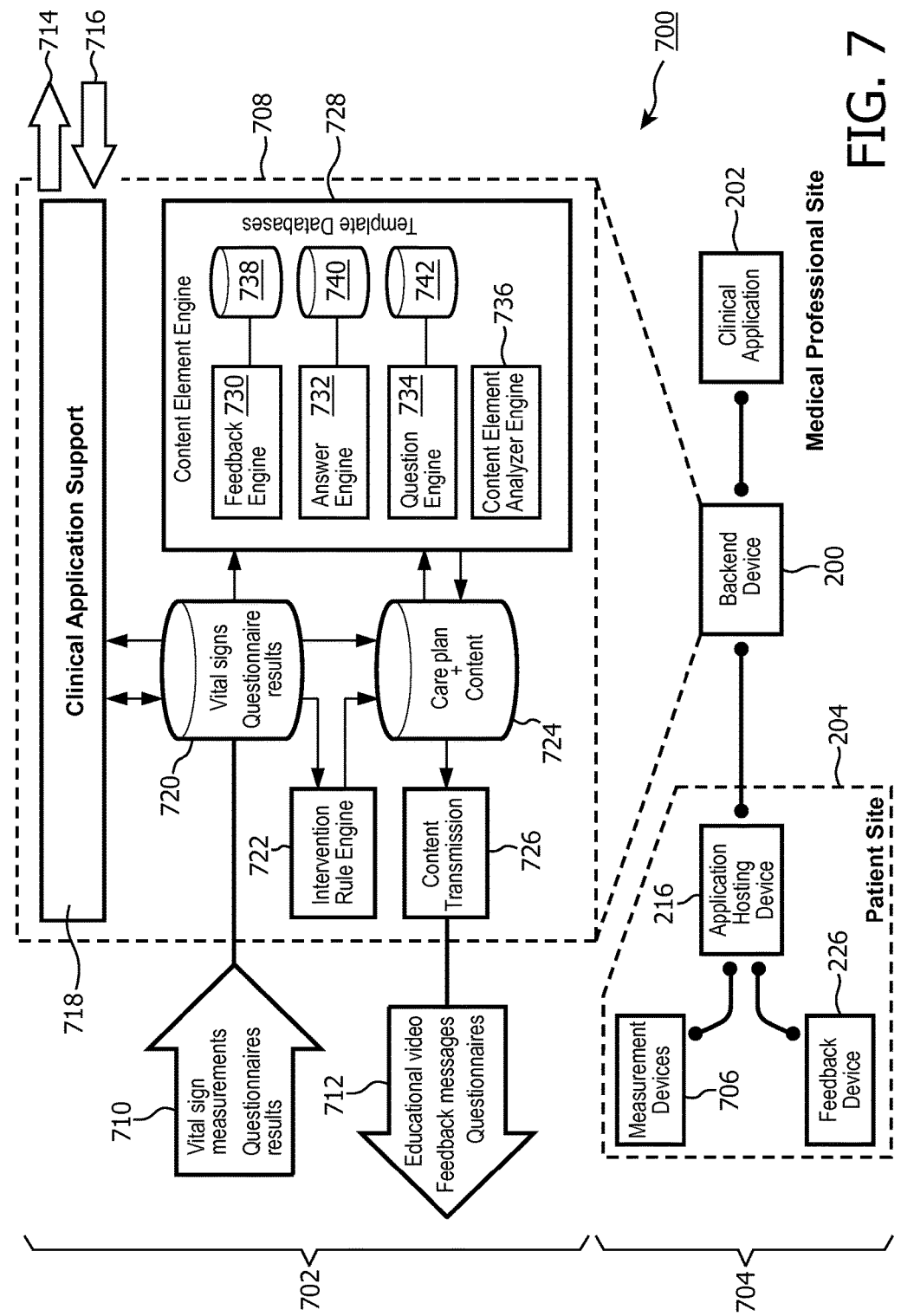
FIG. 7 shows a functional diagram of a remote patient management system according to a further embodiment of the invention.

FIG. 7 shows a functional diagram of a remote patient management system 700 according to an embodiment of the invention. In the top half of FIG. 7 the software components 702 of the computing device 200, which may also be referred to as the backend, of the remote patient management system 700 are shown. In particular the software components and content components 708 of the computing device 200 are the focus of this figure.

In the bottom half of this figure, the hardware components 704 of the remote patient management system 700 are illustrated. As part of the home infrastructure device 204 several diagnostic medical devices 706 are shown as being connected to the application hosting device 216. The hardware components 704 are equivalent to the hardware components illustrated in FIG. 2. These hardware components are not described again here. The software and content components 708 receive input from the home infrastructure device 204. The input 710 may take the form of vital sign measurements and questionnaire results. The home infrastructure device 204 also receives output 712 from the software and content components 708. The output 712 to the home infrastructure device 204 may be educational videos, questionnaires, feedback messages and other content elements. The software and content components 708 also output information 714 to the health professional interface 202. The software and content component 708 also receive input 716 from the health professional interface 202. The output 714 and input 716 from the health professional interface 202 is handled through a clinical application support module 718. The clinical application support module 718 is able to place or gather information from a database 720 which contains vital signs and questionnaire results.

Input 710 from the home infrastructure device 204 may be written into the vital signs and questionnaire results database 720. The vital signs and questionnaire results may also provide input to an intervention rule engine 722. The intervention rule engine analyzes the vital signs and the questionnaire results and may indicate if an intervention with the patient is necessary. The vital signs and questionnaire results database 720 also outputs information to a care plan and content database 724. The care plan and content database outputs care plan and contents to a content transmission module 726. The content transmission module 726 is used to output 712 content elements and care plans to the home infrastructure device 204.

The vital signs and questionnaire results database 720 is able to provide information and data to a content element engine 728. The care plan and content database 724 is able to exchange information with the content element engine 728. The content element engine 728 comprises a content element analyzer engine 736. The content element analyzer engine 736 may comprise code for parsing text into text elements which may be used by a question engine 734, an answer engine 732, and a feedback engine 730. The content element engine 728 further comprises a question engine 734. The question engine 734 uses a question creation template database 742 and parsed text elements in order to construct questions. The content element engine 728 further comprises an answer engine 732. The answer engine 732 uses an answer creation template database 740 and parsed text elements to construct answers to questions. The content element engine 728 further comprises a feedback engine 730 for generating feedback to responses or answers by the patient. The feedback engine 730 is able to create feedback by using an answer feedback template database 738 and parsed text elements.

Figure 8:
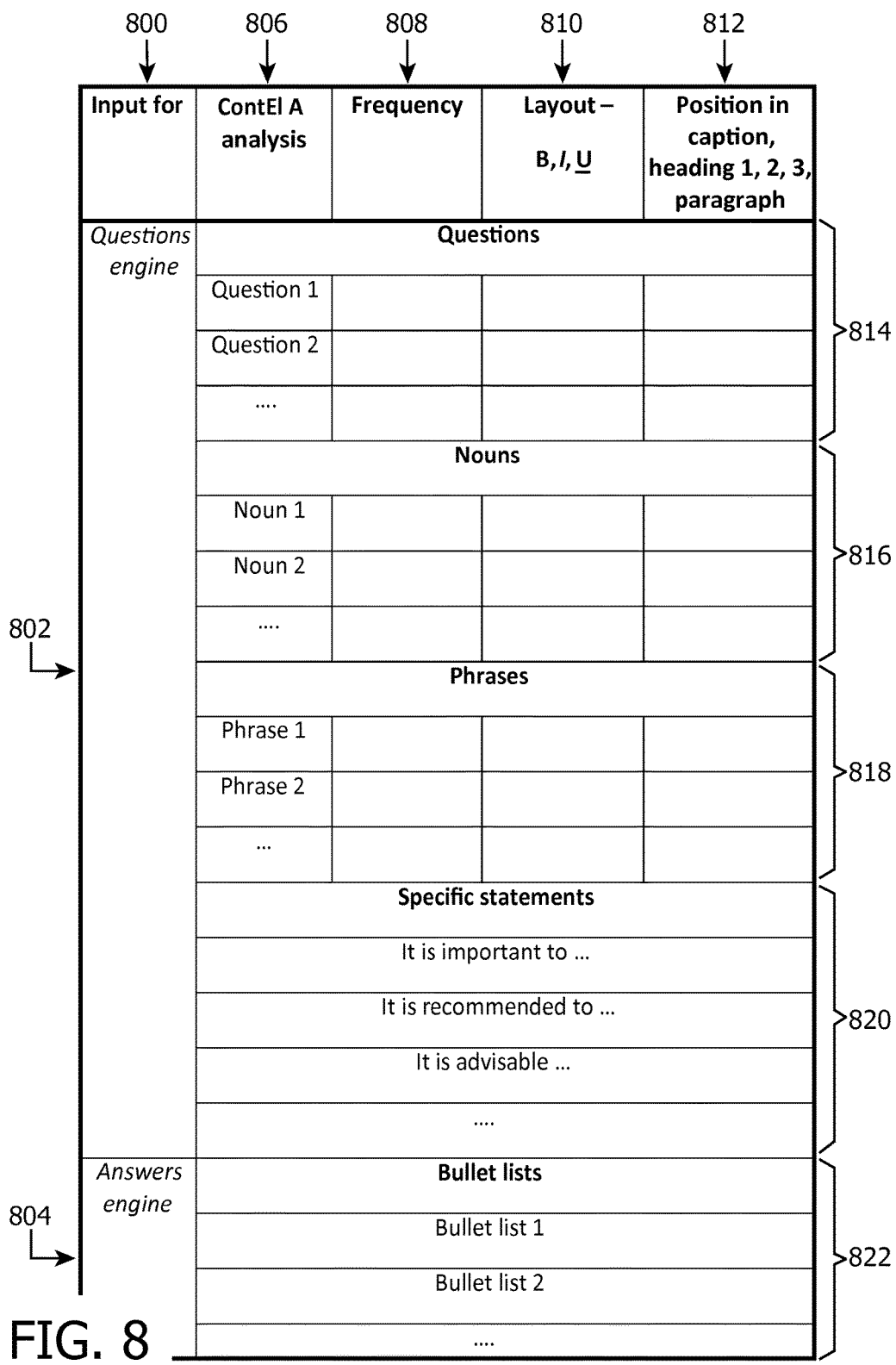
FIG. 8 contains a table which illustrates how the text may be parsed into text elements.

FIG. 8 shows a table which illustrates how the text may be parsed into text elements. This table may be filled by the Content Element Analyzer Engine 736 of FIG. 7. Column 800 indicates the type of input. In this example the input is divided into input to the Question Engine used for generating questions, shown in rows labeled 802, and input to the Answers Engine for generating answers, shown in rows labeled 804. Column 806 contains spaces for the different text elements identified during parsing of the text document. ContEl A refers to the content element of document A, where document A is the text that is parsed. Column 808 indicates the frequency of this text element within the text. Column 810 indicates the layout of the text element, for instance it may be bold, italicized, or underlined in the example for this table. Column 812 indicates the position of the text element. For instance being located in the caption, being located in different headings or being located within the paragraph may be indicated. The text elements may be divided into questions 814, nouns 816, phrases 818, specific statements 820 and bullet lists 822.

An algorithm which may be used to parse the text is:

Step 1 (Scan and Count): The content analyzer engine creates and populates the table of FIG. 8 as follows:
1) Parse content element A (806 of FIG. 8) and detect the most frequently used questions, phrases (fixed combination of nouns, e.g., high blood pressure or heart failure), nouns, specific statements and bullet lists. At this step the rows of Table 3 are generated;
2) For each row fill in the frequency 808, the layout 810 (bold, italic, and underlined) and the position 812 of noun/phrase in the text (a caption, a heading 1, 2, 3, a paragraph, a pane);

Step 2 (Analyze and Select): The content analyzer engine marks the relevant candidates for questions and answers, based on combination of frequency, layout, and position in text.

FIG. 9 is a table which illustrates three different techniques of using templates to construct questions. Column 900 indicates the question number, column 902 indicates a question technique for making questions, and in column 904 examples of questions using technique 902 are given. In row 906 question template technique QT1 is illustrated. Technique QT1 is reusing the selected questions from the analyzer table either without any changes or rephrasing. Essentially questions identified in the text are used directly. Row 908 illustrates question templating technique 2 abbreviated QT2. In technique QT2, a selected phrase or a noun from the analyzer table is used in a template. In row 910 technique question template technique 3 is illustrated, abbreviated QT3. In this technique a selected statement from the analyzer table is reformulated into a question.

The table of FIG. 9 illustrates how a question engine may be implemented. The questions engine could generates a number of questions, based on the result of the content analyzer engine, to check the effect of ContEl A (806 of FIG. 8) on the patient's knowledge. Examples of algorithms that the questions engine may use, but are not limited to; are:

QT 1. Reusing the selected questions from the analyzer table either without any changes or without being rephrased;

QT 2. Using a selected phrase or a noun from the analyzer table in a template, e.g., "What does it mean <phrase/noun>?" or "What is <phrase/noun >?" or a statement in a template, e.g., "How relevant is the following <statement> for you?"

QT 3. Reformulating a selected statement from the analyzer table into a question.

FIG. 10 shows an example of a template which may be used for creating answers to questions. Column 1000 corresponds to a particular question. The label for the question in column 1000 corresponds to the label in column 900 of FIG. 9. Column 1002 shows the answer number. Column 1004 indicates the template technique used for creating the answer. Column 1006 shows examples of templates for answer text. Column 1008 indicates the purpose of the answer. Column 1010 indicates a possible value which could be used in the calculation of the assessment score. The rows indicated 1012 correspond to answer template technique number 1 which is abbreviated AT1. For this templating technique a multi-choice template is used to answer closed questions generated by the question engine. The rows indicated by numeral 1014 use answer template technique number 2. This is abbreviated AT2. In this technique a multi-choice template is used to answer open questions generated by the question engine. In the rows labeled 1016 answer template technique number 3 abbreviated AT3 is used. In answer template technique number 3 multi-choice answers are taken from a bullet list in the analyzer table which was generated by the content analyzer engine.

The technique illustrated in FIG. 10 may be implemented as an answer engine, which may use the following techniques or algorithms for generating answers:

AT 1. Use a multi-choice template, e.g., "True/False/I don't know" or "Yes/No/I don't know", to answer close questions generated by the question engine;

AT 2. Use a multi-choice template, e.g., "True answer/False answer/I don't know", "Very important/Important/Neutral/Unimportant/Very unimportant" or "Statement 1/Statement 2/ . . . /Statement m" to answer open questions generated by the question engine. The Statement 1, 2, . . . , m are taken from the specific statements in the content analyzer table. ContEl A.

AT 3. Use multi-choice answers taken from a bullet list in the analyzer table generate by the content analyzer engine.

FIG. 11 shows an example of a template used for creating feedback to answers. In column 1100 is a list of questions. The label in column 1100 corresponds to the labels in column 1000 in FIG. 10 and column 900 in FIG. 9. Column 1102 contains the template for the answer text. Column 1104 contains the feedback number. This is simply a label for the feedback. Column 1106 contains a label which indicates which feedback templating technique is being used. The templating techniques are detailed below. Column 1108 contains examples of feedback text using the templating technique indicated in column 1106. Column 1110 is text which indicates the purpose of the feedback given in the corresponding row of column 1108.

Feedback may be generated in one of two ways. Either first as a feedback per answer of a question; It's applicable primary for a teaching quiz. Second a feedback for the complete questionnaire based on the knowledge level of the patient may be generated.

Algorithms or templating techniques for generating feedbacks are illustrated by, but not limited to:

FT 1. For a correct answer use a combination of a template, e.g., "That is right!/Well done!/Very good!" to reward the correct answer and then reinforce the knowledge by summing up the answer.

FT 2. For a partly correct answer use a combination of a template, e.g., "That is partly right!/Good!" to reward the partly correct answer and then reinforce the knowledge by summing up the fully correct answer.

FT 3. For an incorrect answer attract patient's attention and then provide the fully correct answer to educate the patient.

FT 4. For "I don't know" answer summarize the question and provide fully correct answer to educate the patient.

FIGS. 12a and 12b contain a table identical to that shown in FIG. 8 that has been filled with text elements that have been parsed from pages 44 and 45 of the workbook: "The Heart Failure Plan," Bob Lewin, Jill Pattenden, Julie Ferguson, and Helen Roberts, published and copyrighted by the British Heart Foundation in 2005.

FIGS. 13a-13f show a table which shows a newly generated quiz created using the text elements from the table of FIGS. 12a and 12b. Column 1300 indicates a question number. Column 1302 indicates answer number for a particular question number 1300. Column 1304 indicates the templating technique used for creating the answers. The abbreviations used in FIGS. 13a-13f correspond to the abbreviations used in FIGS. 9, 10, and 11. FIGS. 13a-13f is intended to illustrate how the techniques of FIGS. 9-11 may be used to generate a quiz. Column 1306 contains the text of a particular answer 1302. Each answer also has feedback which is presented to the patient. Column 1308 contains the feedback number and in parenthesis the feedback technique or template used for generating the feedback. Column 1310 contains the feedback which corresponds to the answer in the same row in column 1306. If a patient selected a particular answer then column 1312 indicates the next question that should be posed to the patient. Column 1314 indicates the score of a particular answer. This score may be used in calculating the assessment score.

Additional embodiments of the invention may also include:

A content element simulator: The simulator (pre-view of the survey/quiz) would allow for offline simulation of different answer-paths, including an overall quiz evaluation and possible follow-up actions. It's an additional tool that the medical professionals could use to pre-test the survey/quiz via a simulation.

A content element edutainment simulator: It would replace the conventional questionnaires with interactive assessments enabling the transformation from surveys and teaching quizzes to interactive dialogs in virtual environment empowered by interactive media. Entertainment elements leading to edutainment (education+entertainment) will be a powerful tool to gather subjective information.

A content element scheduler: It schedules a newly generated content element such as a survey or a quiz in the patients specific care plan. The purpose of the generated questionnaire can be either 1) checking the knowledge level or 2) the changes therein triggered by a content element A (806 of FIG. 8). Purpose 1) requires filling in the questionnaire a couple of days after a content element A (806 of FIG. 8) is shown to the patients, while purpose 2) requires pre-post assessment. In both cases the content element scheduler can schedule the content element at the right time.

To assess a patient's parameter with the survey or quiz coupled to a given content element A (806 of FIG. 8) before a content element A (806 of FIG. 8) is exposed to the patients. In this way, first the problems are identified with a patient's parameter (e.g., shortcomings in the patients knowledge), and second only selected parts of a content element A (806 of FIG. 8) are exposed to the patients addressing his/her shortcomings. This aspect of the ID allows for creation of a tailored patient's care plan.

Providing additional attribute to each content element indicating desired complexity of the assessment, i.e., max number of questions, survey vs. teaching quiz, and etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

LIST OF REFERENCE NUMERALS 200 computing device
202 health professional interface
204 home infrastructure device
206 patient
208 scale
210 blood pressure cuff
212 blood sugar measurement device
214 blood sample
216 application hosting device
218 processor
220 memory
222 care plan
224 assessment content element
226 feedback device
228 display
230 graphical user interface
232 assessment question
234 possible answers with checkboxes
236 submit answer button
238 processor
240 storage
242 memory
244 content element
246 assessment content element
248 assessment content element creation module
250 text-to-speech module
252 optical character registration module
254 speech-to-text module
256 vital sign trend tracking module
258 patient record
260 multi-media content library
262 care plan library
700 remote patient management system
702 software components
704 hardware components
706 diagnostic medical devices
708 software and content components
710 input from home infrastructure device
712 output to home infrastructure device
714 input from health professional interface
716 output to health professional interface
718 clinical application support module
720 vital sign and questionnaire response database
722 intervention rule engine
724 care plan and content database
726 content transmission module
728 content element engine
730 feedback engine
732 answer engine
734 question engine
736 content element analyzer engine
738 answer response template database
740 answer creation template database
742 question creation template database

The invention claimed is:

1. A remote patient management system, the system comprising:
one or more processors programmed to:
receive content selection input provided by a physician;
deliver, in response to the content selection input, a content element to a patient associated with the patient's care plan selected by the physician, wherein the content element includes a list of assessment parameters which indicate a behavioral effect of the content element on the patient's compliance with the content element;
generate an assessment content element using the list of assessment parameters of the content element and the text of the content element by:
parsing the text into text elements;
determining a frequency of each of the text elements;
selecting a candidate for question creation using the frequency of each of the text elements; and
generating a question to create the assessment content element using the candidate and by reusing a question parsed from the text;
deliver the assessment content element to the patient;
receive a response from the patient responding to the assessment content element; and
calculate an assessment score using the response; and
a home infrastructure device, wherein the home infrastructure device includes:
a diagnostic medical device for measuring a value of a patient vital sign; and
wherein the list of assessment parameters is appended with a supplementary assessment parameter in response to the value of the vital sign measurement being outside of a predetermined range;

a voice to text generation module for at least partially generating the text on any audio components of the content element; and an optical character recognition module for at least partially generating the text on any image components of the content element.

2. The remote patient management system of claim 1, wherein the step of generating an assessment content element further includes:

determining an emphasis for each of the text elements;
determining a position for each of the text elements; and
wherein the step of selecting a candidate for question creation using the frequency of each of the text elements includes:
using the emphasis and position for each of the text elements for the selection.

3. The remote patient management system of claim 1, wherein the step of generating an assessment content element further includes:

generating a set of multiple choice answers for each of the questions.

4. The remote patient management system of claim 3, wherein the set of multiple choice answers is generated using at least one of:

a multi-choice template for answering closed questions;
a multi-choice template for answering open questions; and
multiple choice answers generated from a bullet list detected during parsing the text into text elements.

5. The remote patient management system of claim 3, wherein the step of generating an assessment content element further includes:

generating a feedback element for each answer of the set of multiple choice answers.

6. The remote patient management system of claim 5, wherein the feedback content element is generated using any one of the following:

a correct answer feedback template;
a partially correct answer feedback template;
an incorrect answer feedback template; and
an "I don't know" answer feedback template.

7. The remote patient management system of claim 1, wherein the text elements include at least one of: questions, phrases, nouns, specific statements, and bullet lists.

8. The remote patient management system of claim 1, wherein a text to voice generation module further generates the assessment content element.

9. The remote patient management system of claim 1, wherein the remote patient management system further includes:

a feedback device for providing feedback based upon the response.

10. The remote patient management system of claim 1, wherein the assessment content element is a quiz or a survey.

11. The remote patient management system of claim 1, wherein the assessment score is a measure of at least one of: knowledge, self-care behavior, compliance, and beliefs on barriers and benefits.

12. The remote patient management system of claim 1, wherein the content element includes games-for-health, and symptoms checklists.

13. The remote patient management system of claim 1, wherein the remote patient management system further includes:

a home infrastructure device, wherein the home infrastructure device includes:

a diagnostic medical device for measuring a value of a vital sign;
wherein calculation of the assessment score is based at least partially on a trend of the value of the vital sign.

14. A method of calculating an assessment score using a computing device with a processor, the method comprising instructions executable by the processor for:

receiving content selection input provided by a physician;
delivering, in response to the content selection input, the content element to the patient associated with the patient's care plan selected by the physician, wherein the content element includes a list of assessment parameters which indicate a behavioral effect of the content element on the patient's compliance with the content element;
receiving a measured value of a patient's vital sign from a diagnostic medical device, wherein the list of assessment parameters is appended with a supplementary assessment parameter if the value of the vital sign measurement is outside compliance with the content element;
generating an assessment content element using the list of assessment parameters and the text of the content element including:
partially generating text on any audio components of the content element;
partially generating text on any image components of the content element;
parsing the text into text elements;
determining a frequency of each of the text elements;
determining an emphasis for each of the text elements;
determining a position for each of the text elements, wherein the position indicates that a text element is located in one of:
a caption;
a heading; or
paragraph;
selecting a candidate for question creation using the frequency, emphasis, and position of each of the text elements; and
generating a question to create the assessment content element using the candidate;
delivering the assessment content element to the patient;
receiving a response from the patient responding to the assessment content element; and
calculating the assessment score using the response.

15. The remote patient management system of claim 1, wherein the content element includes at least three of: a message, a tip, an interactive message, a medical video, a psychological video, a heart failure goal module, a diabetes goal module, games-for-health, symptoms checklists, recipes, and an educational game.

16. The remote patient management system of claim 1, wherein the content element includes recipes.

17. The remote patient management system of claim 3, wherein the set of multiple choice answers is generated using all of:

a multi-choice template for answering closed questions;
a multi-choice template for answering open questions; and
multiple choice answers generated from a bullet list detected during parsing the text into text elements.

18. The method according to claim 14, wherein the content element includes at least three of: a tip, an interactive message, a medical video, a psychological video, a heart failure goal module, a diabetes goal module, games-for-health, symptoms checklists, recipes, and an educational game.

19. The method according to claim 14, further including indicating that a text element is relevant in response to the positon of the text element indicating that the text element is located in a heading.

\* \* \* \* \*